(12) United States Patent
Lefebvre et al.

(10) Patent No.: US 12,161,557 B2
(45) Date of Patent: Dec. 10, 2024

(54) STEMLESS HUMERAL ANCHORING COMPONENT FOR A SHOULDER PROSTHESIS HUMERAL IMPLANT

(71) Applicant: SHOULDER FRIENDS INSTITUTE, Paris (FR)

(72) Inventors: Yves Lefebvre, Strasbourg (FR); Stephane Audebert, Blecourt (FR); Johannes Barth, Meylan (FR); Christophe Charousset, Paris (FR); Jerome Garret, Limonest (FR); David Gallinet, Geneuille (FR); Arnaud Godeneche, Saint Cyr Au Mont d'Or (FR); Jacques Guery, Nevers (FR); Thierry Joudet, Libourne (FR)

(73) Assignee: SHOULDER FRIENDS INSTITUTE, Paris (FR)

( * ) Notice: Subject to any disclaimer, the term of this patent is extended or adjusted under 35 U.S.C. 154(b) by 30 days.

(21) Appl. No.: 18/313,673

(22) Filed: May 8, 2023

(65) Prior Publication Data
US 2023/0270557 A1    Aug. 31, 2023

Related U.S. Application Data

(63) Continuation of application No. 16/886,107, filed on May 28, 2020, now abandoned, which is a continuation of application No. PCT/FR2018/052994, filed on Nov. 27, 2018.

(30) Foreign Application Priority Data

Nov. 28, 2017 (FR) ..................... 17/61299

(51) Int. Cl.
*A61F 2/40* (2006.01)
*A61F 2/30* (2006.01)

(52) U.S. Cl.
CPC .......... *A61F 2/4014* (2013.01); *A61F 2/4003* (2013.01); *A61F 2002/3021* (2013.01); *A61F 2002/30616* (2013.01); *A61F 2002/30884* (2013.01); *A61F 2002/30894* (2013.01);
(Continued)

(58) Field of Classification Search
CPC ............ A61F 2/4003; A61F 2002/4007; A61F 2002/4022
See application file for complete search history.

(56) References Cited

U.S. PATENT DOCUMENTS

2006/0009852 A1* 1/2006 Winslow ............ A61B 17/1684
623/19.14
2016/0324648 A1* 11/2016 Hodorek ............... A61F 2/4059
2019/0105169 A1* 4/2019 Sperling ............... A61F 2/4003

* cited by examiner

*Primary Examiner* — Megan Y Wolf
(74) *Attorney, Agent, or Firm* — Burris Law, PLLC (57) ABSTRACT

A method for securing a stemless humeral includes positioning the stemless humeral anchoring component to the humerus such that a lateral anchoring wing extends in a direction of a lateral side of the humerus into a lateral region and two medial anchoring wings face a medial side of the humerus in a medial region. The lateral region has a lower bone density relative to the medial region. The stemless humeral anchoring component is positioned eccentrically such that the anchoring stud and the two medial anchoring wings are anchored in the medial region. The stemless humeral anchoring component is secured in resected proximal epiphyseal and metaphyseal portions of the humerus without reaching a diaphyseal portion of the humerus.

20 Claims, 4 Drawing Sheets

(52) U.S. Cl.
CPC ................ *A61F 2002/4022* (2013.01); *A61F 2002/4085* (2013.01)

STEMLESS HUMERAL ANCHORING COMPONENT FOR A SHOULDER PROSTHESIS HUMERAL IMPLANT

CROSS-REFERENCE TO RELATED APPLICATIONS

This application is a continuation of U.S. application Ser. No. 16/886,107, filed on May 28, 2020, which is a continuation of International Application No. PCT/FR2018/052994, filed on Nov. 27, 2018, which claims priority to and the benefit of FR 17/61299, filed on Nov. 28, 2017. The disclosures of the above applications are incorporated herein by reference.

FIELD

The present disclosure relates to a stemless humeral anchoring component for a shoulder prosthesis humeral implant.

BACKGROUND

The statements in this section merely provide background information related to the present disclosure and may not constitute prior art.

A stemless humeral anchoring component, also called "stemless humeral component," is a component provided for an anchoring in the resected proximal epiphyseal and metaphyseal portions of the humerus without using an anchoring stem implanted in the diaphyseal portion of the humerus, and more specifically in the medullary cavity of the humerus.

In order to make such stemless humeral anchoring components, it is known from the documents FR 2 980 685, FR 2 997 290 and EP 2 474 288 to use a conical, cylindrical or dome-shaped anchoring part provided with peripheral teeth around its entire perimeter, and it is also known from the document EP 2 815 726 to use an anchoring cup having flexible lateral segments separated by slots, some of the segments having protruding lugs, and others having recessed notches.

The state of the art can also be illustrated by the teaching of the document EP 2 830 541 which describes a stemless humeral anchoring component provided with a circular flange, a hollow sleeve and cantilevered protruding toothed tabs of the circular flange, as well as by the teaching of the document EP 2 663 263 which discloses a stemless humeral anchoring component provided with a crown having a lower face from which a plurality of perforated and sharp blades protrudes.

A stemless humeral anchoring component is also known from the document EP 2 965 720, including an anchoring stud secured to four anchoring wings extending radially along the periphery of the anchoring stud and angularly spaced by an angle of 90 degrees, these wings being moreover integral with a proximal crown surrounding the anchoring stud.

The state of the art can also be illustrated by the teachings of the documents U.S. Patent Publication No. 2013/0018476 and WO 2013/009407 which discloses a stemless humeral anchoring component including an anchoring stud secured to six anchoring wings distributed radially and symmetrically along the periphery of the anchoring stud.

All these stemless humeral anchoring components of the prior art have the drawback of being able to be positioned essentially in a central bone area of the resected epiphyseal and metaphyseal portions of the humerus, which is a cancellous bone area where the bone density does not provide an optimal torsional stability for the stemless humeral anchoring component.

SUMMARY

This section provides a general summary of the disclosure and is not a comprehensive disclosure of its full scope or all of its features.

The present disclosure provides a stemless humeral anchoring component which is shaped to provide an increased torsional stability.

To this end, the present disclosure provides a stemless humeral anchoring component for a shoulder prosthesis humeral implant, this stemless humeral anchoring component including an anchoring stud secured to anchoring wings extending radially along the periphery of the anchoring stud, where this stemless humeral anchoring component is remarkable in that the anchoring wings are three in number and comprise one lateral anchoring wing and two medial anchoring wings, wherein the anchoring wings are angularly spaced by an angle between 110 and 130 degrees, and wherein the lateral anchoring wing has a radially measured length greater than the radially measured lengths of the medial anchoring wings.

Thus, thanks to this shaping, the lateral anchoring wing is provided to extend into the lateral region towards the greater tubercle, while the two medial anchoring wings are provided to extend in the medial region close to Merkel's spur with high bone density. The Merkel's spur, also called medial calcar, is a medial region originating from the cortex, that is to say from the peripheral portion of the bone, and extending inwardly, such a medial or Merkel region having an increased bone density which provides a particularly stable support of the two medial anchoring wings and therefore an increased torsional stability. The lateral anchoring wing is intended to extend in the lateral region and it is longer, which allows offsetting the anchoring stud and the medial anchoring wings so that they extend in the medial region (or area) with a higher bone density. Indeed, the longer lateral anchoring wing will promote this offset of the stemless humeral anchoring component in the direction of the medial area with a higher bone density, in other words by bringing the anchoring stud and the medial anchoring wings closer together towards the medial side, which allows having an anchoring of the anchoring stud and the medial anchoring wings in the medial or Merkel area.

According to one feature, the anchoring wings are angularly spaced by an angle of 120 degrees ±2 degrees.

This symmetrical angular distribution of the anchoring wings further promotes the torsional stability.

According to a variant, the ratio between the length of the lateral anchoring wing and the length of a medial anchoring wing is between 1.1 and 1.3, and in particular between 1.1 and 1.2.

According to a variant, the anchoring stud is a body of revolution centered on a central axis, and the lengths of the anchoring wings are measured radially from this central axis, and the length of each lateral anchoring wing is between 15 and 25 millimeters, and in particular between 17 and 21 millimeters, and the length of a medial anchoring wing is between 11.5 and 22.5 millimeters, and in particular between 14.5 and 19 millimeters.

In one particular form, the two medial anchoring wings have the same radially measured length, for an equivalent symmetrical support of these two medial anchoring wings in the medial area.

Advantageously, the anchoring wings are perforated, to promote an osseointegration or bone regeneration inside the perforations of the anchoring wings.

According to a variant, the anchoring wings and/or the anchoring stud are covered externally and at least partially with a porous or rough metal surface coating promoting an osseointegration.

Advantageously, the porous or rough metal coating is a two-layer coating comprising a layer of porous or rough titanium or of a porous or rough titanium alloy, and a layer of calcium phosphate, such as calcium hydroxyapatite.

In another particular form, each anchoring wing comprises:
- a rectilinear segment extending radially from a peripheral proximal portion of the anchoring stud; and
- a curved segment connecting a termination of the rectilinear segment to a peripheral distal portion of the anchoring stud.

According to one possibility of the present disclosure, the peripheral proximal portion of the anchoring stud, from which the rectilinear segments of the anchoring wings protrude, is formed of a peripheral proximal end edge of the anchoring stud.

Thus, the proximal end edge of the anchoring stud and the rectilinear segments of the anchoring wings are coplanar, to provide an increased freedom for the surgeon in positioning the stemless humeral anchoring component.

According to another possibility of the present disclosure, the peripheral distal portion of the anchoring stud, from which the curved segments of the anchoring wings protrude, is formed of a peripheral distal end edge of the anchoring stud.

Thus, the distal end edge of the anchoring stud is extended radially by the curved segments of the anchoring wings, to promote the insertion or depression of the stemless humeral anchoring component.

In accordance with another advantageous feature of the present disclosure, the anchoring stud is hollow by being provided with an inner orifice, to facilitate the manipulation during the anchoring operation and also to facilitate the fastening of the humeral insert on the stemless humeral anchoring component.

According to one feature, the inner orifice has a frustoconical proximal hole extended by a tapped hole, optionally followed by a distal through hole, where the frustoconical proximal hole is used for fastening a Morse taper of the humeral insert, the tapped hole is used, if desired, to extract the stemless humeral anchoring component by means of an extraction tool screwed into this tapped hole.

According to another feature, the anchoring stud has a generally frustoconical shape.

The present disclosure concerns a shoulder prosthesis humeral implant, comprising a stemless humeral anchoring component according to the present disclosure, and a humeral insert fastened on the stemless humeral anchoring component and having:
- a hemispherical cap shaped for a joint with a glenosphere of a glenoid implant; or
- a spherical joint head (otherwise called a humeral head) shaped for a joint on a joint body of a glenoid implant.

The present disclosure also relates to a shoulder prosthesis comprising a humeral implant as described above, and a glenoid implant comprising:
- a glenosphere shaped for a joint with the hemispherical cap of the humeral insert; or
- a joint body shaped for a joint with the spherical joint head of the humeral insert.

The present disclosure also concerns a range of stemless humeral anchoring components comprising several stemless humeral anchoring components according to the present disclosure and having distinct sizes.

In another form, the present disclosure provides a method for securing a stemless humeral anchoring component in a humerus. The stemless humeral anchoring component comprises an anchoring stud secured to anchoring wings extending radially along a periphery of the anchoring stud. The anchoring wings comprise a lateral anchoring wing and two medial anchoring wings. The anchoring wings being angularly spaced by an angle between 110 and 130 degrees. The lateral anchoring wing having a length greater than a length of each medial anchoring wing and the two medial anchoring wings have the same length. The method includes positioning the stemless humeral anchoring component to the humerus such that the lateral anchoring wing extends in a direction of a lateral side of the humerus into a lateral region and the two medial anchoring wings face a medial side of the humerus in a medial region. The lateral region has a lower bone density relative to the medial region. The stemless humeral anchoring component is positioned eccentrically such that the anchoring stud and the two medial anchoring wings are anchored in the medial region. The stemless humeral anchoring component is secured in resected proximal epiphyseal and metaphyseal portions of the humerus without reaching a diaphyseal portion of the humerus.

In variations of the method of the above paragraph, which can be implemented individually or in any combination: the method further includes guiding the stemless humeral anchoring component in the humerus with a guide pin; an orientation of the anchoring wings is adjustable on the guide pin; the method further includes adjusting an orientation of the anchoring wings prior to securing the stemless humeral anchoring component to the humerus; a ratio between the length of the lateral anchoring wing and the length of one medial anchoring wing of the two medial anchoring wings is between 1.1 and 1.3; the anchoring wings are angularly spaced by an angle of 120 degrees; the anchoring wings are perforate; each anchoring wing comprises a rectilinear segment extending radially from a peripheral proximal portion of the anchoring stud and a curved segment connecting a termination of the rectilinear segment to a peripheral distal portion of the anchoring stud; the anchoring stud is hollow and defines an inner orifice; the inner orifice is configured to receive a guide pin to guide the stemless humeral anchoring component in the humerus; the inner orifice extends through the anchoring stud; the inner orifice has a frustoconical proximal hole extended by a tapped hole; and the anchoring stud has a frustoconical shape.

In yet another form, the present disclosure provides a method for securing a stemless humeral anchoring component in a humerus. The stemless humeral anchoring component comprises an anchoring stud defining an inner orifice and secured to anchoring wings extending radially along a periphery of the anchoring stud. The anchoring wings comprise a lateral anchoring wing and two medial anchoring wings. The anchoring wings being angularly spaced by an angle between 110 and 130 degrees. The lateral anchoring wing having a length greater than a length of each medial anchoring wing and the two medial anchoring wings have the same length. The method includes guiding the stemless humeral anchoring component in the humerus using a guide pin extending through the inner orifice and positioning the stemless humeral anchoring component in the humerus such that the lateral anchoring wing extends in a direction of a lateral side of the humerus into a lateral region and the two medial anchoring wings face a medial side of the humerus in a medial region. The lateral region has a lower bone density relative to the medial region. The stemless humeral anchoring component is positioned eccentrically such that the anchoring stud and the two medial anchoring wings are anchored in the medial region. The stemless humeral anchoring component is secured in resected proximal epiphyseal and metaphyseal portions of the humerus without reaching a diaphyseal portion of the humerus.

In variations of the method of the above paragraph, which can be implemented individually or in any combination: the method further includes removing the guide pin after the stemless humeral anchoring component is positioned in the humerus; the inner orifice has a frustoconical proximal hole extended by a tapped hole; an orientation of the anchoring wings is adjustable on the guide pin; the anchoring wings are perforated; and the anchoring stud has a frustoconical shape.

In yet another form, the present disclosure provides a method for securing a stemless humeral anchoring component in a humerus. The stemless humeral anchoring component comprises an anchoring stud defining an inner orifice and secured to anchoring wings extending radially along a periphery of the anchoring stud. The anchoring wings comprise a lateral anchoring wing and two medial anchoring wings. The anchoring wings being angularly spaced by an angle between 110 and 130 degrees. The lateral anchoring wing having a length greater than a length of each medial anchoring wing and the two medial anchoring wings have the same length. The method includes guiding the stemless humeral anchoring component in the humerus using a guide pin extending through the inner orifice, positioning the stemless humeral anchoring component in the humerus such that the lateral anchoring wing extends in a direction of a lateral side of the humerus into a lateral region and the two medial anchoring wings face a medial side of the humerus in a medial region, and removing the guide pin after the stemless humeral anchoring component is positioned in the humerus. The stemless humeral anchoring component is positioned eccentrically such that the anchoring stud and the two medial anchoring wings are anchored in the medial region. The stemless humeral anchoring component is secured in resected proximal epiphyseal and metaphyseal portions of the humerus without reaching a diaphyseal portion of the humerus. An orientation of the anchoring wings is adjustable on the guide pin. The lateral region has a lower bone density relative to the medial region.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

With reference to FIGS. 1 to 5, a stemless humeral anchoring component 1 according to the present disclosure is a one-piece component made of a metal material and which comprises an anchoring stud 2 secured to three anchoring wings 3, 4 extending radially along the periphery of the anchoring stud 2.

The anchoring stud 2 is a body of revolution centered on a central axis 20 and having a peripheral wall 21 of a generally frustoconical shape having two opposite peripheral end edges:

a peripheral proximal end edge 22; and
a peripheral distal end edge 23.

The anchoring stud 2 has a generally frustoconical shape in the direction of a narrowing starting from the peripheral proximal end edge 22 to the peripheral distal end edge 23.

The anchoring stud 2 is hollow and defines an inner orifice 24 of revolution centered on the central axis 20 and opening on the side of the peripheral proximal end edge 22 and having successively a frustoconical proximal hole 25 extended by a tapped hole 26, and optionally followed by a distal hole 27 (shown in the form of FIG. 8) opening on the side of the peripheral distal end edge 23.

Figure 1:
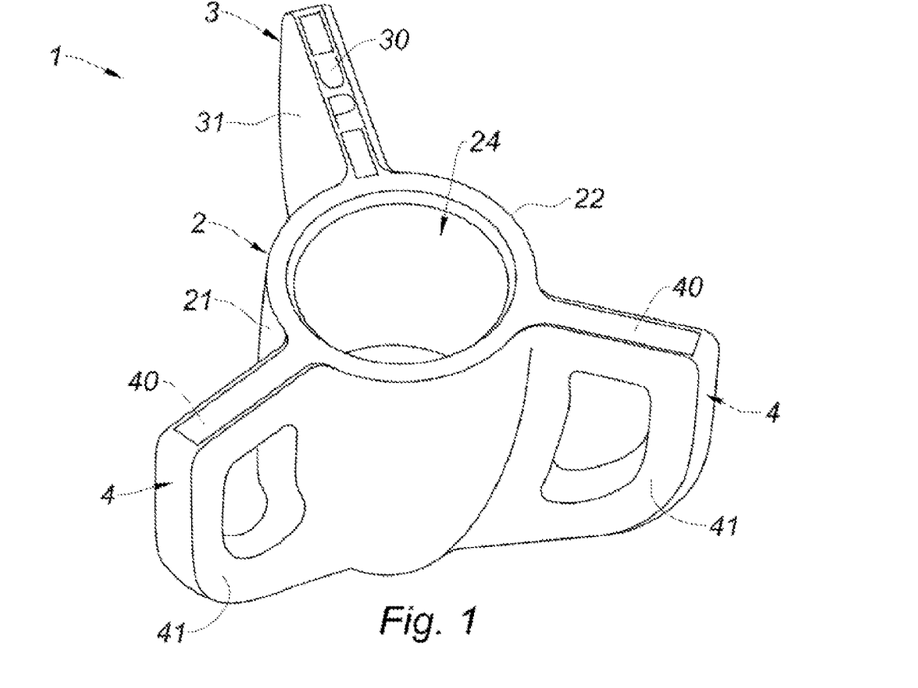
FIG. 1 is a schematic perspective view of a stemless humeral anchoring component according to the present disclosure.
Figure 2:
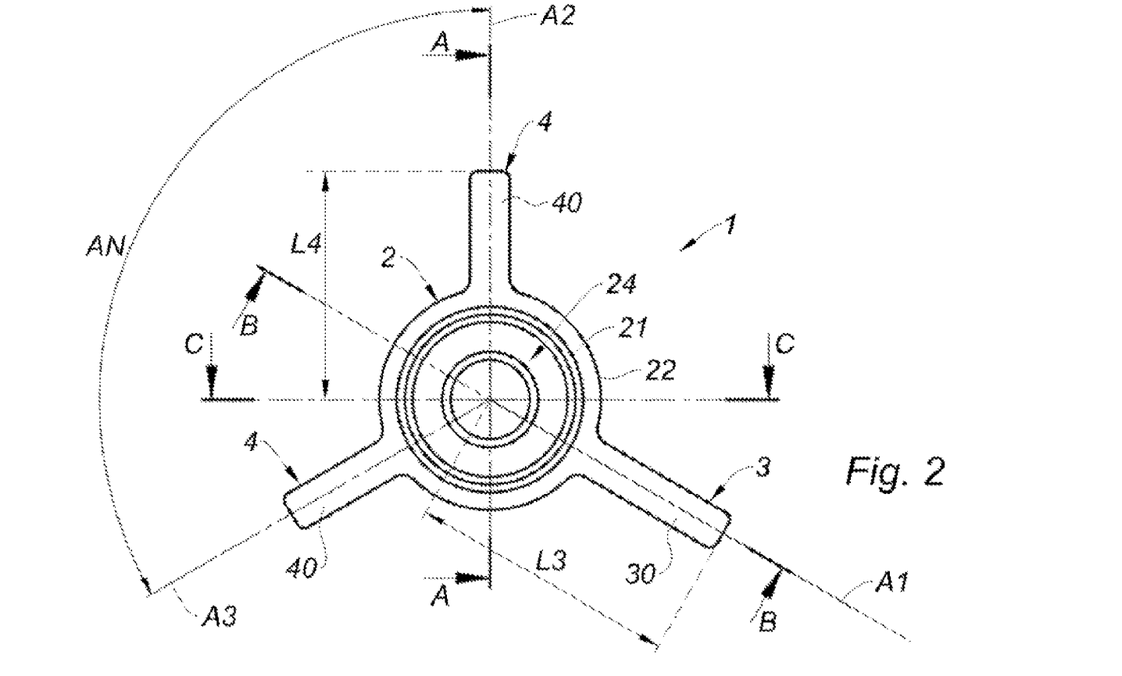
FIG. 2 is a schematic top view of the stemless humeral anchoring component of FIG. 1.

The anchoring wings 3, 4 extend radially along radial axes A1, A2, A3 intersecting on the central axis 20. The anchoring wings 3, 4 protrude externally from the peripheral wall 21 of the anchoring stud 2 and extend in planes including the central axis 20 and the radial axes A1, A2, A3.

The anchoring wings 3, 4 are angularly spaced by an angle AN between 110 and 130 degrees, and in one form, by an angle AN of 120 degrees ±2 degrees (that is to say between 118 and 122 degrees). In other words, each anchoring wing 3, 4 is angularly spaced from each other anchoring wing 3, 4 by such an angle AN. In FIG. 2, only one angle AN, of the three angles, is illustrated, for clarity. The angles AN can be measured between the radial axes A1, A2, A3.

The anchoring wings 3, 4 comprise a lateral anchoring wing 3 and two medial anchoring wings 4, where the lateral anchoring wing 3 has a radially measured length L3 greater than the radially measured length L4 of each medial anchoring wings; the two medial anchoring wings 4 have the same radially measured length L4.

Figure 3:
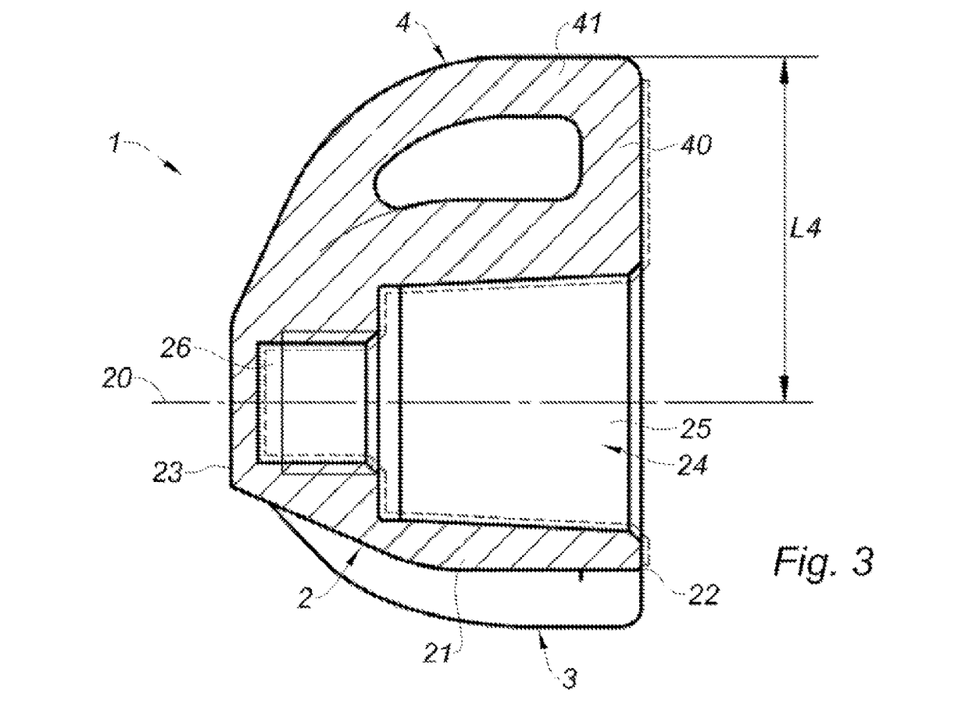
FIG. 3 is a schematic cross-sectional view of the stemless humeral anchoring component according to the section plane A-A shown in FIG. 2.
Figure 4:
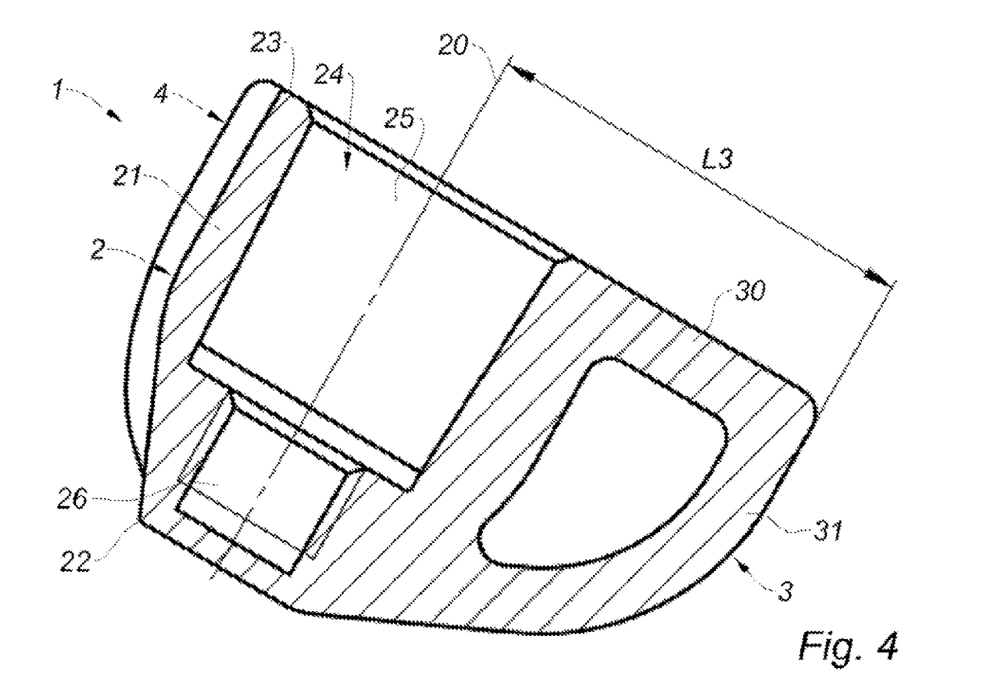
FIG. 4 is a schematic cross-sectional view of the stemless humeral anchoring component according to the section plane B-B shown in FIG. 2.
Figure 5:
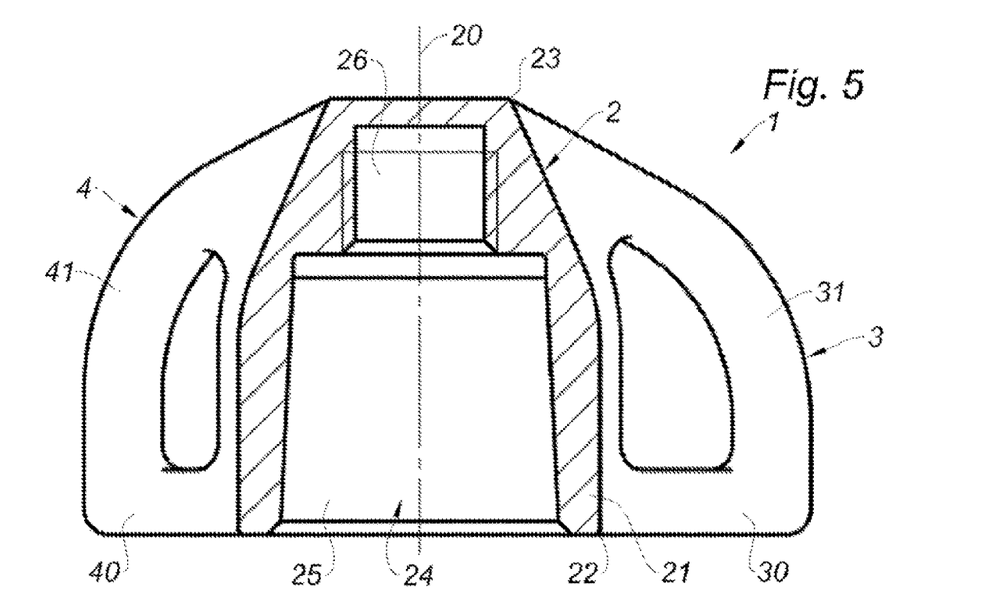
FIG. 5 is a schematic cross-sectional view of the stemless humeral anchoring component according to the section plane C-C shown in FIG. 2.

These lengths L3 and L4 are measured starting from the central axis 20 along the respective radial axes A1, A2, A3, as shown in FIGS. 2 to 4.

The ratio between the length L3 of the lateral anchoring wing 3 and the length L4 of a medial anchoring wing 4 among the two medial anchoring wings 4 is between 1.1 and 1.2. The length L3 of the lateral anchoring wing 3 is between 17 and 21 millimeters, and the length L4 of a medial anchoring wing 4 is between 14.5 and 19 millimeters.

The anchoring wings 3, 4 are perforated, to promote an osseointegration and, as such, each anchoring wing 3, 4 comprises:
- a rectilinear segment 30; 40 extending radially from the peripheral proximal end edge 22 of the anchoring stud 2; and
- a curved segment 31; 41 connecting a termination of the rectilinear segment 30; 40 to a peripheral distal end edge 23 of the anchoring stud 2.

Thus, each anchoring wing 3, 4 may extend over the entire height (distance measured along the central axis 20) of the anchoring stud 2.

The anchoring wings 3, 4 and the anchoring stud 2 are externally covered with a porous or rough metal surface coating promoting an osseointegration, such as for example a two-layer coating comprising a layer of porous or rough titanium or of a porous or rough titanium alloy, and a layer of calcium phosphate, such as calcium hydroxyapatite.

Figure 6:
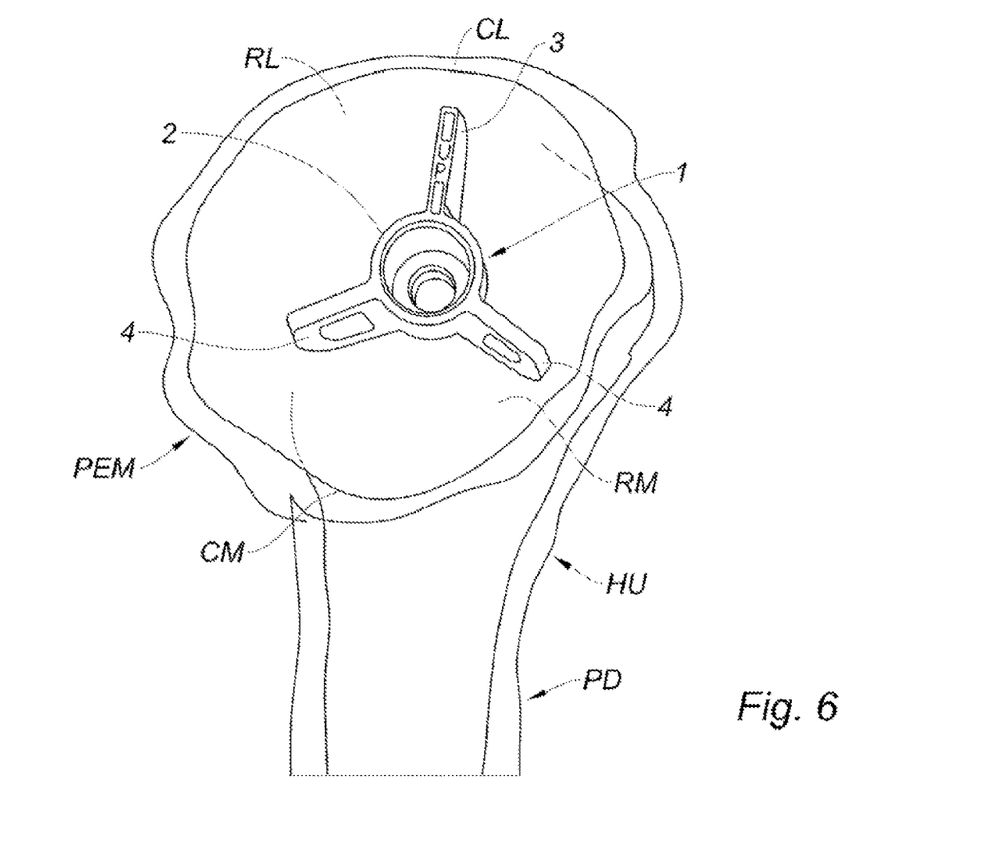
FIGS. 6 and 7 are schematic views of the stemless humeral anchoring component of FIG. 1 implanted in a humerus.
Figure 7:
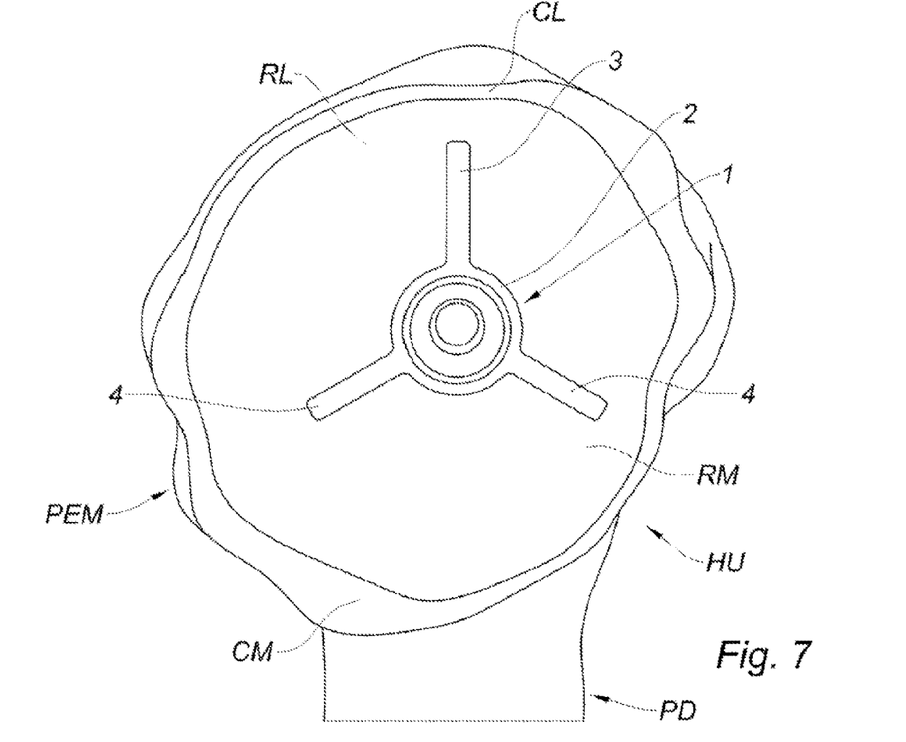

As shown in FIGS. 6 and 7, the stemless humeral anchoring component 1 provides an anchoring in the resected proximal epiphyseal and metaphyseal portions PEM of the humerus HU, without reaching the diaphyseal portion PD of the humerus HU.

The stemless humeral anchoring component 1 is positioned such that:
- the lateral anchoring wing 3 extends in the direction of the lateral side CL of the humerus HU, in the direction of the greater tubercle into the lateral region RL with a lower bone density compared to the medial region RM,
- the two medial anchoring wings 4 are facing the medial side CM of the humerus HU to extend into the medial region RM of the Merkel's spur with a high bone density.

More specifically, the stemless humeral anchoring component 1 is positioned eccentrically, in the sense that the latter is brought closer towards the medial side CM mainly due to the increased length of the lateral anchoring wing 3 which promotes this eccentricity, and therefore by bringing closer the anchoring stud 2 and the medial anchoring wings 4 towards the medial side CM, which allows having the medial anchoring wings 4 which extend almost integrally in the medial region RM also called medial calcar, thus providing a support mainly in the medial region RM with a high bone density, while the lateral anchoring wing 3 extends almost integrally in the lateral region RL of a cancellous bone.

In order to facilitate guiding the stemless humeral anchoring component 1 to its final implantation position, as illustrated in FIGS. 6 and 7, the surgeon can use a guide pin which cooperates with the inner orifice 24, such that the surgeon begins by positioning the guide pin and then slides the anchoring stud 2 on this guide pin to the final implantation position, and the guide pin is then removed. The use of a guide pin leaves the possibility of adjusting the right orientation of the anchoring wings 3, 4, by orienting the lateral anchoring wing 3 in the direction of the lateral side CL, in other words in the direction of the greater tubercle.

Thus, thanks to this shaping of the stemless humeral anchoring component 1 and thanks to this implantation, a particularly stable support of the medial anchoring wings 4 in the medial region RM with an increased bone density is provided, and therefore an increased overall stability for the stemless humeral anchoring component 1.

Figure 8:
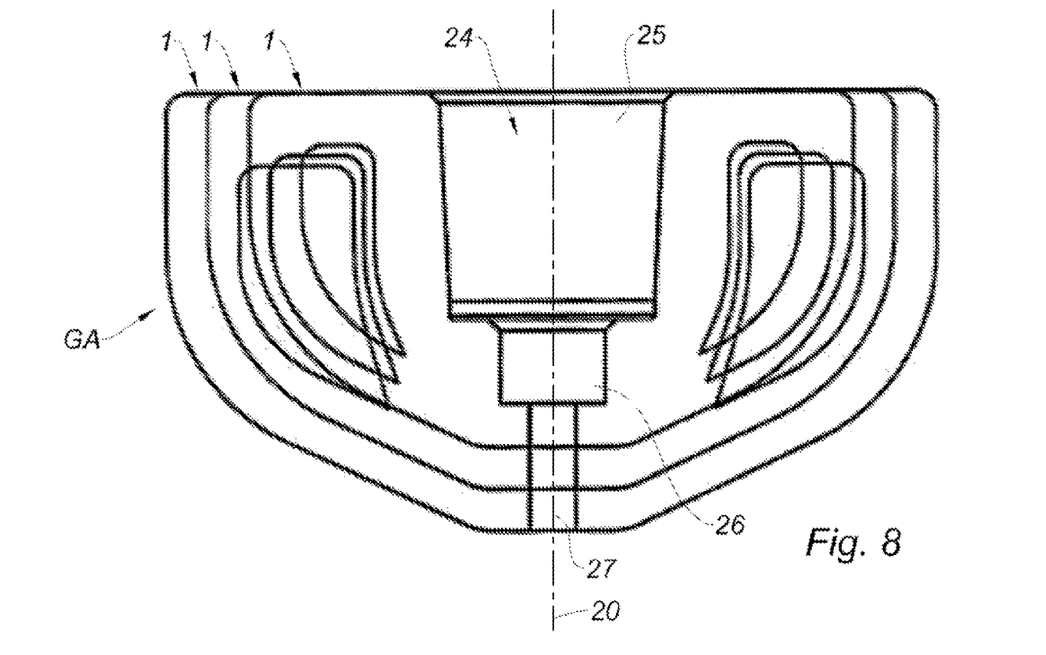
FIG. 8 is a schematic cross-sectional view along the section plane C-C and in superposition of three stemless humeral anchoring components belonging to a range according to the present disclosure.

As shown in FIGS. 8, this stemless humeral anchoring component 1 can be declined within a range GA comprising a plurality of stemless humeral anchoring components 1 having distinct (different) sizes, and in particular having heights (dimensions measured along the central axis), lengths (radially measured dimensions) and thicknesses for the segments of the anchoring wings which increase with the size. However, the dimensions of the inner orifice 24 remain identical from one size to another.

Of course, the example of implementation mentioned above is in no way limiting and other improvements and details can be made to the stemless humeral anchoring component according to the present disclosure, without departing from the scope of the present disclosure where other types of porous or rough coating can for example be considered, or else other forms of inner orifice can be provided.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method for securing a stemless humeral anchoring component in a humerus, the stemless humeral anchoring component comprises an anchoring stud secured to anchoring wings extending radially along a periphery of the anchoring stud, the anchoring wings comprise a lateral anchoring wing and two medial anchoring wings, the anchoring wings being angularly spaced by an angle between 110 and 130 degrees, and the lateral anchoring wing having a length greater than a length of each medial anchoring wing, and wherein the two medial anchoring wings have the same length, the method comprising:
   positioning the stemless humeral anchoring component to the humerus such that the lateral anchoring wing extends in a direction of a lateral side of the humerus into a lateral region and the two medial anchoring wings face a medial side of the humerus in a medial region, the lateral region has a lower bone density relative to the medial region,
   wherein the stemless humeral anchoring component is positioned eccentrically such that the anchoring stud and the two medial anchoring wings are anchored in the medial region, the stemless humeral anchoring component secured in resected proximal epiphyseal and metaphyseal portions of the humerus without reaching a diaphyseal portion of the humerus.

2. The method of claim 1, further comprising guiding the stemless humeral anchoring component in the humerus with a guide pin.

3. The method of claim 2, wherein an orientation of the anchoring wings is adjustable on the guide pin.

4. The method of claim 1, further comprising adjusting an orientation of the anchoring wings prior to securing the stemless humeral anchoring component to the humerus.

5. The method of claim 1, wherein a ratio between the length of the lateral anchoring wing and the length of one medial anchoring wing of the two medial anchoring wings is between 1.1 and 1.3.

6. The method of claim 1, wherein the anchoring wings are angularly spaced by an angle of 120 degrees.

7. The method of claim 1, wherein the anchoring wings are perforated.

8. The method of claim 1, wherein each anchoring wing comprises:
a rectilinear segment extending radially from a peripheral proximal portion of the anchoring stud; and
a curved segment connecting a termination of the rectilinear segment to a peripheral distal portion of the anchoring stud.

9. The method of claim 1, wherein the anchoring stud is hollow and defines an inner orifice.

10. The method of claim 9, wherein the inner orifice is configured to receive a guide pin to guide the stemless humeral anchoring component in the humerus.

11. The method of claim 9, wherein the inner orifice extends through the anchoring stud.

12. The method of claim 9, wherein the inner orifice has a frustoconical proximal hole extended by a tapped hole.

13. The method of claim 1, wherein the anchoring stud has a frustoconical shape.

14. A method for securing a stemless humeral anchoring component in a humerus, the stemless humeral anchoring component comprises an anchoring stud defining an inner orifice and secured to anchoring wings extending radially along a periphery of the anchoring stud, the anchoring wings comprise a lateral anchoring wing and two medial anchoring wings, the anchoring wings being angularly spaced by an angle between 110 and 130 degrees, and the lateral anchoring wing having a length greater than a length of each medial anchoring wing, and wherein the two medial anchoring wings have the same length, the method comprising:
guiding the stemless humeral anchoring component in the humerus using a guide pin extending through the inner orifice; and
positioning the stemless humeral anchoring component in the humerus such that the lateral anchoring wing extends in a direction of a lateral side of the humerus into a lateral region and the two medial anchoring wings face a medial side of the humerus in a medial region, the lateral region has a lower bone density relative to the medial region,
wherein the stemless humeral anchoring component is positioned eccentrically such that the anchoring stud and the two medial anchoring wings are anchored in the medial region, the stemless humeral anchoring component secured in resected proximal epiphyseal and metaphyseal portions of the humerus without reaching a diaphyseal portion of the humerus.

15. The method of claim 14, further comprising removing the guide pin after the stemless humeral anchoring component is positioned in the humerus.

16. The method of claim 14, wherein the inner orifice has a frustoconical proximal hole extended by a tapped hole.

17. The method of claim 14, wherein an orientation of the anchoring wings is adjustable on the guide pin.

18. The method of claim 14, wherein the anchoring wings are perforated.

19. The method of claim 14, wherein the anchoring stud has a frustoconical shape.

20. A method for securing a stemless humeral anchoring component in a humerus, the stemless humeral anchoring component comprises an anchoring stud defining a frustoconical-shaped inner orifice and secured to anchoring wings extending radially along a periphery of the anchoring stud, the anchoring wings comprise a lateral anchoring wing and two medial anchoring wings, the anchoring wings being angularly spaced by an angle between 110 and 130 degrees, and the lateral anchoring wing having a length greater than a length of each medial anchoring wing, and wherein the two medial anchoring wings have the same length, the method comprising:
guiding the stemless humeral anchoring component in the humerus using a guide pin extending through the inner orifice;
positioning the stemless humeral anchoring component in the humerus such that the lateral anchoring wing extends in a direction of a lateral side of the humerus into a lateral region and the two medial anchoring wings face a medial side of the humerus in a medial region, the lateral region has a lower bone density relative to the medial region; and
removing the guide pin after the stemless humeral anchoring component is positioned in the humerus,
wherein the stemless humeral anchoring component is positioned eccentrically such that the anchoring stud and the two medial anchoring wings are anchored in the medial region, the stemless humeral anchoring component secured in resected proximal epiphyseal and metaphyseal portions of the humerus without reaching a diaphyseal portion of the humerus, and
wherein an orientation of the anchoring wings is adjustable on the guide pin.

* * * * *